(12) United States Patent
Kullik et al.

(10) Patent No.: US 7,481,221 B2
(45) Date of Patent: Jan. 27, 2009

(54) BREATHING MASK WITH INTEGRATED SUCTION AREA

(75) Inventors: Götz Kullik, Lübeck (DE); Hans-Ullrich Hansmann, Barnitz (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 443 days.

(21) Appl. No.: 11/253,539

(22) Filed: Oct. 19, 2005

(65) Prior Publication Data
US 2006/0102184 A1    May 18, 2006

(30) Foreign Application Priority Data
Nov. 17, 2004    (DE)    ........................ 10 2004 055 433

(51) Int. Cl.
A62B 18/08    (2006.01)
A62B 18/00    (2006.01)
A62B 18/02    (2006.01)
A61M 15/00    (2006.01)
A61M 16/00    (2006.01)

(52) U.S. Cl. ............................ 128/207.11; 128/200.27; 128/204.18; 128/205.25; 128/206.27; 128/204.11

(58) Field of Classification Search ............ 128/201.22, 128/202.18, 206.19, 201.23, 201.29, 205.25, 128/206.13, 206.27, 207.11, 207.17, 207.18, 128/DIG. 26, 846, 869
See application file for complete search history.

(56) References Cited

U.S. PATENT DOCUMENTS

| | | | | |
|---|---|---|---|---|
| 1,463,390 A * | 7/1923 | Fernandes | ................... | 128/863 |
| 2,897,817 A * | 8/1959 | Marina | ................... | 128/205.17 |
| 3,625,207 A * | 12/1971 | Agnew | ................... | 128/206.28 |
| 3,804,086 A * | 4/1974 | Agnew | ................... | 128/202.19 |
| 3,955,570 A * | 5/1976 | Hutter, III | ............... | 128/201.23 |
| 4,194,247 A * | 3/1980 | Melander | ........................ | 2/457 |
| 4,469,097 A * | 9/1984 | Kelman | ................. | 128/205.22 |
| 4,848,366 A * | 7/1989 | Aita et al. | .................... | 128/863 |
| 4,951,662 A * | 8/1990 | Townsend, Jr. | .......... | 128/205.25 |
| 5,033,128 A * | 7/1991 | Torres | ........................... | 2/427 |
| 5,046,492 A * | 9/1991 | Stackhouse et al. | .... | 128/200.27 |
| 5,584,286 A * | 12/1996 | Kippax | .................... | 128/200.24 |
| 5,694,927 A * | 12/1997 | Bohmfalk | .............. | 128/206.19 |
| 6,443,153 B1 * | 9/2002 | Viljanen et al. | ........ | 128/205.25 |

FOREIGN PATENT DOCUMENTS

DE        102 10 878 A1    10/2003

* cited by examiner

Primary Examiner—Justine R Yu
Assistant Examiner—Annette F Dixon
(74) Attorney, Agent, or Firm—McGlew & Tuttle, P.C.

(57) ABSTRACT

A breathing mask for breathing support devices (10) to guide the breathing support gas to the patient. The mask includes a mask body including a material that is permeable to air at least in partial areas. A gas guiding structure is provided which can be connected to suction openings of the breathing support device (10). The gas guiding structure extends through the interior of the mask body. The gas guiding structure for the transport/delivery of gas is limited partially by air-permeable areas of the wall of the mask body, through which ambient air can be drawn in. The mask is characterized by high wear comfort and improved safety against accidental coverage of the suction areas.

20 Claims, 2 Drawing Sheets

BREATHING MASK WITH INTEGRATED SUCTION AREA

CROSS REFERENCE TO RELATED APPLICATIONS

This application claims the benefit of priority under 35 U.S.C. § 119 of German Application 10 2004 055 433.1 filed Nov. 17, 2004, the entire contents of which are incorporated herein by reference.

FIELD OF THE INVENTION

The present invention pertains to a breathing mask with integrated suction area for breathing support devices to be worn by the patient.

BACKGROUND OF THE INVENTION

A possible application of such breathing masks is represented by so-called CPAP (continuous positive airway pressure) respirators. Patients who require breathing support for various reasons, for example, sleep apnea or COPD (chronic obstructive pulmonary disease), are frequently treated with such CPAP respirators. A settable overpressure for supporting the respiration is made available here to the patient. The supply is usually with constant pressure over the entire breathing cycle, the pressure set being made available for a breathing mask. These breathing masks are usually designed as nose or mouth-and-nose masks, which are connected with flexible tubes for supplying breathing gas, via which the supply takes place from a CPAP device. The air to be breathed in is drawn in for this purpose by the CPAP device usually through a filter arranged in the front and is sent under a slight overpressure into the flexible supply tubes. The breathing air breathed out usually escapes through an expiration valve, which is frequently directly integrated with the mask. In addition, a humidifier or a combined heat/humidity exchanger may be optionally present. The devices are frequently designed such that the breathing gas must be led over rather long flexible tubes.

Acceptance of the auxiliary means used, which is determined by the comfort, safety and problem-free integration in everyday life, is especially important in case of applications whose consistent implementation is extensively the responsibility of the user.

If longer flexible tubes are used to guide the breathing gas, these must have a considerable cross section with a diameter of approx. 15 mm to 20 mm in order to have tolerable flow resistances. A desired constancy of the pressure in the area of a patient's nose can be achieved only if pressure measurement is performed in the mask or if the pneumatic resistance of the flexible tubes is kept so low that the pressure drop is sufficiently low in case of the volume flows necessary for the desired breathing support. An additional signal is to be transmitted pneumatically or electrically in case of pressure measurement in the mask. Furthermore, highly dynamic adjustment of the pressure source in the breathing support device is necessary. This increases the technical effort and consequently the costs. Moreover, the flexible tubes hinder the mobility of the user of the mask. Furthermore, the flexible tubes create a highly technical impression and thus compromise the recognizability of the patient's face with its characteristic zones, especially the area around the eyes. As a result, an inhibition threshold may be built up, which prevents regular use in everyday life.

There have been attempts at arranging portable devices for breathing support close to the patient in order to eliminate the above-mentioned drawbacks. A device of this class has been known from DE 102 10 878 A1. A miniaturized breathing support device with a suction filter was integrated directly in a mask body in this device.

A breathing support device carried by the patient also must meet high requirements concerning safety besides the requirements in terms of overall size, weight, the avoidance of noise and energy supply.

The risk of coverage of the suction openings represents a possible source of error and a safety risk especially for breathing support during sleep. This also applies to devices according to the state of the art which are integrated in the mask body.

SUMMARY OF THE INVENTION

The object of the present invention is to provide a breathing mask for breathing support devices with high wear comfort and high safety against accidental coverage of the suction opening, which said breathing support devices are to be worn by the patient.

Some of the CPAP devices currently available are so advanced in terms of their type of construction, their noise generation and their energy consumption that it is possible to wear these devices in an adapted form directly at the patient. The advantage of such devices is the elimination of the mobility restriction and that it is possible to integrate the gas routing into a device and mask combination.

The present invention provides a breathing mask for breathing support devices worn by the patient, comprising a mask body consisting of a material that is permeable to air at least in partial areas, wherein means for the transport/delivery of gas, which can be connected to suction openings of a breathing support device, extend through the interior of the mask body. The means for the transport/delivery of gas end at areas of the wall of the mask body, which are permeable to air and through which ambient air can be drawn in. The gas transport/delivery means are made and fastened airtightly in relation to the interior of the mask body. The areas of the wall of the mask body, through which the ambient air can be drawn in, may advantageously consist of a material that has a filtering action in relation to the air being drawn in.

The breathing air needed is drawn in according to the present invention in the vicinity of the nose of a patient and fed to a breathing support device via closed channels. From there, it can be sent under a slight overpressure into the interior of the mask body. For example, various flexible tubes may be provided as channels for the transport/delivery of gas. The introduction into the interior breathing area of the mask body may take place, for example, continuously with a slight overpressure.

The breathing support device may be located in the immediate vicinity of the mask body, which may be designed as a nose mask, a mouth/nose mask or as a face mask. Preferred positions for arranging the breathing support device are located in the nape or shoulder area of the patient.

In such a device, the breathing gases can be transported/delivered from the site at which they are drawn in to the breathing support device and from there into the interior of the mask body fully or partially within a correspondingly dimensioned strap, which is used at the same time to attach the mask body to the patient's head. Flexible tubes or gas-tight channels may be integrated within the strap for this purpose. It is advantageous if the strap comprises areas that have a multilayer design and at least two layers of the material of the strap that are located one on top of another are connected to one another such that they form a channel, which is used as a means for the transport/delivery of the air drawn in from the mask body to a breathing support device being worn close to the body. It is especially advantageous if the strap comprises, besides, means for the transport/delivery of breathing gases from the breathing support device into the interior of the mask body, for example, in the form of additional ducts. The gas guide can be integrated in the strap on both sides of the mask or of the head and may be designed such that each side has a sufficient capacity to guarantee trouble-free breathing gas supply. It is advantageous for this purpose if the strap comprises at least two channels each on different sides of the head, the cross section of the channels being variable. This can be advantageously embodied by the use of flexible textile materials for forming the channels. The maximum cross section of the channels should be at least so large that the breathing mask supply can be ensured through the channels on one side of the head alone.

The gases breathed out are removed through conventional expiration valves or alternative solutions, for example, through areas in the limiting surface of the mask body, which are permeable to air and through which expiratory breathing masks can escape into the environment.

The breathing gas is drawn in according to the present invention in the vicinity of the patient's nose such that the drawing in is likewise carried out through gas-permeable areas in the limiting surface of the mask body. These areas, which can be considered to be a modified suction opening for the breathing mask, form an integral part of the mask body and are used at the same time to limit the interior of the mask from the ambient space.

It is advantageous if the limiting surface of the mask body is made at least partially of a textile, gas-permeable structure. As a result, a possibly desired filter action can be achieved as a result in the area acting as a suction opening in a very simple manner.

The gas-permeable part of the mask surface intended for the drawing in according to the present invention advantageously limits a contiguous volume area in the interior of the mask body, which cannot communicate with the rest of the interior space of the mask, but is connected to means that permit the transport/delivery of gas to the breathing mask, i.e., the air drawn in, to the breathing support device. It may be formed by conventional flexible tubes or gas-tight channels made of textile materials.

In an advantageous embodiment, the separated volume area in the interior of the mask is limited by a flexible wall, which is impermeable to air. To maintain the ability of this volume area to function, it is advantageous if the mask body comprises a shaping support frame, to which the material that forms the outer limitation of the mask body is attached, the support frame being located in the area of the air-impermeable flexible wall between the air-impermeable flexible wall and the material that forms the outer limitation of the mask body. As a result, parts of the support frame can ensure a sufficient distance between the limiting surfaces and prevent the vacuum prevailing during the drawing in of ambient air from narrowing the volume area intended for the drawing in, in the interior of the mask to the extent that suction is hindered.

It is especially practical if the air-permeable areas of the wall of the mask body, through which ambient air can be drawn in, are arranged along the edge of the mask body in the vicinity of the contact area with the user's face. As a result, different directions of suction can be automatically achieved, as a result of which complete coverage of the entire suction area becomes nearly impossible. Moreover, if the areas through which the expiratory breathing gases can escape into the environment are located mainly in the middle area of the mask body, there is good uncoupling between the air flow being drawn in and the air flow being released.

Due to the mask body being worn in the vicinity of the nose, the position of the suction area corresponds extensively to the area from which the breathing air is also drawn in during natural breathing without auxiliary means. As a result, the usual safety measures and reflexes of the patient can be utilized. For example, it is highly unlikely that an adult would hinder his breathing by constricting his own nose due to the unfavorable position of the face. After a brief discomfort, he would rather turn his face to the side in order to make unhindered breathing possible. The accidental coverage of the areas of the mask body that are relevant for the drawing in of breathing air can be prevented from occurring by the same reflexes when these areas are arranged sufficiently close to the patient's nose. The dimensioning and the limitation of the suction area as an integrated air filter may make the use of additional filters unnecessary, which means increased wear comfort.

The present invention will be explained in greater detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
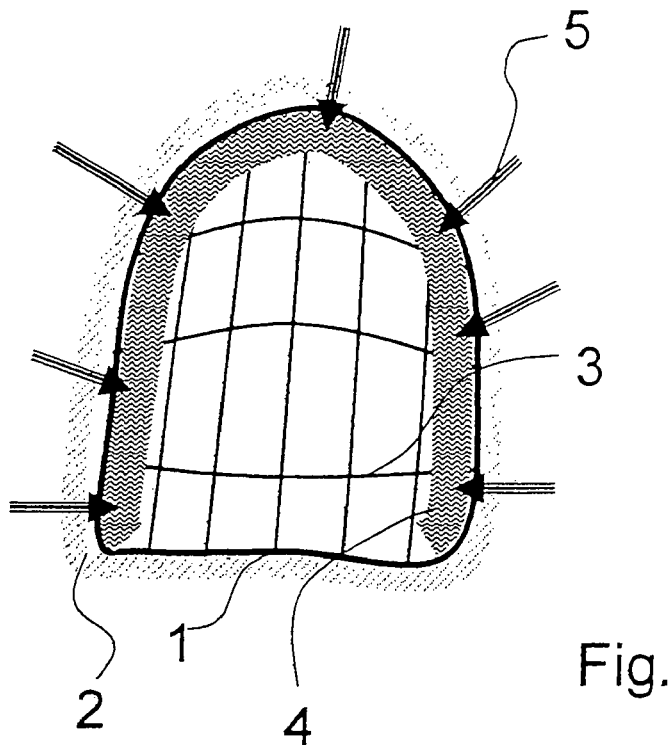
FIG. 1 is a schematic view of a mask body according to the present invention.

Referring to the drawings in particular, FIG. 1 shows a schematic view of the inner side of a mask body according to the present invention. A nasal CPAP mask has a fixed frame 1. This frame extends approximately in parallel to the contact surface of the mask on the face. On the patient side, this frame 1 carries a flexible, very soft seal 2, which is supported by the inner pressure of the mask. The frame 1 is provided with a grid-like skeleton as a shaping support frame 3, which approximately predetermines the three-dimensional shape of the mask. An air-permeable textile fabric, which also acts as a filter in the suction area 4 located close to the frame, is drawn over this skeleton on the outer side of the mask body. The ambient air is drawn in according to the present invention over the entire area 4, illustrated by the arrows 5. The rest of the surface of the mask body is available for the discharge of the expiratory breathing gases into the environment.

Figure 2:
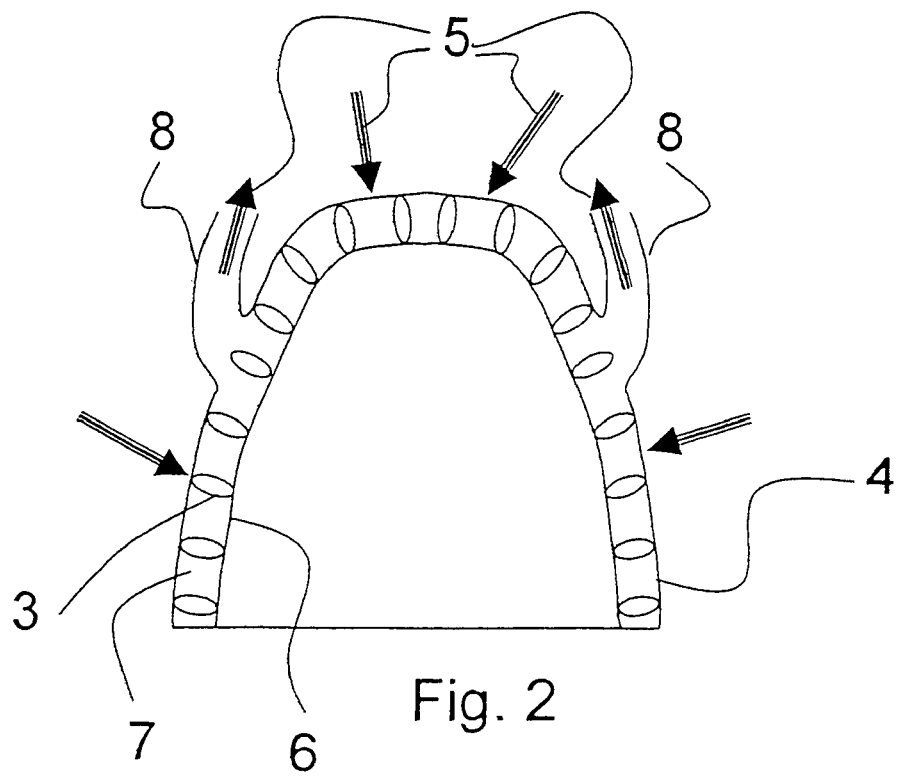
FIG. 2 is a schematic sectional view through a mask body according to the present invention to illustrate the flow conditions.

FIG. 2 shows a schematic sectional view through the same mask body according to the present invention with a section plane close to the frame. A non-permeable flexible wall 6, which limits a volume area 7, through which the ambient air drawn in is sent, toward the rest of the interior space of the mask (breathing area), is arranged on the inner side of the shaping support frame 3. This volume area 7 comprises a flat chamber between the mask surface and the interior space of the mask and ensures the uniform distribution of the suction volume flow over the entire suction area 4. Parts of the shaping support frame 3 also ensure a sufficient distance between the non-permeable flexible wall 6 and the air-permeable fabric in the suction area 4 close to the frame in case of vacuum during the drawing in of ambient air. The volume area 7 is connected to channels 8 leading away laterally for guiding the gas, through which the ambient air drawn in reaches a breathing support device.

The embodiment according to the present invention prevents expired air from entering the suction area. Due to the geometry of the suction area 4, flat distribution of the suction volume flow is achieved, which means high tolerance of partial coverage and low noise generation. The different orientations of the air-permeable surfaces in the suction area 4 and in the central or breathing area of the mask body additionally ensure good uncoupling between the inspiratory and expiratory air flows.

Figure 3:
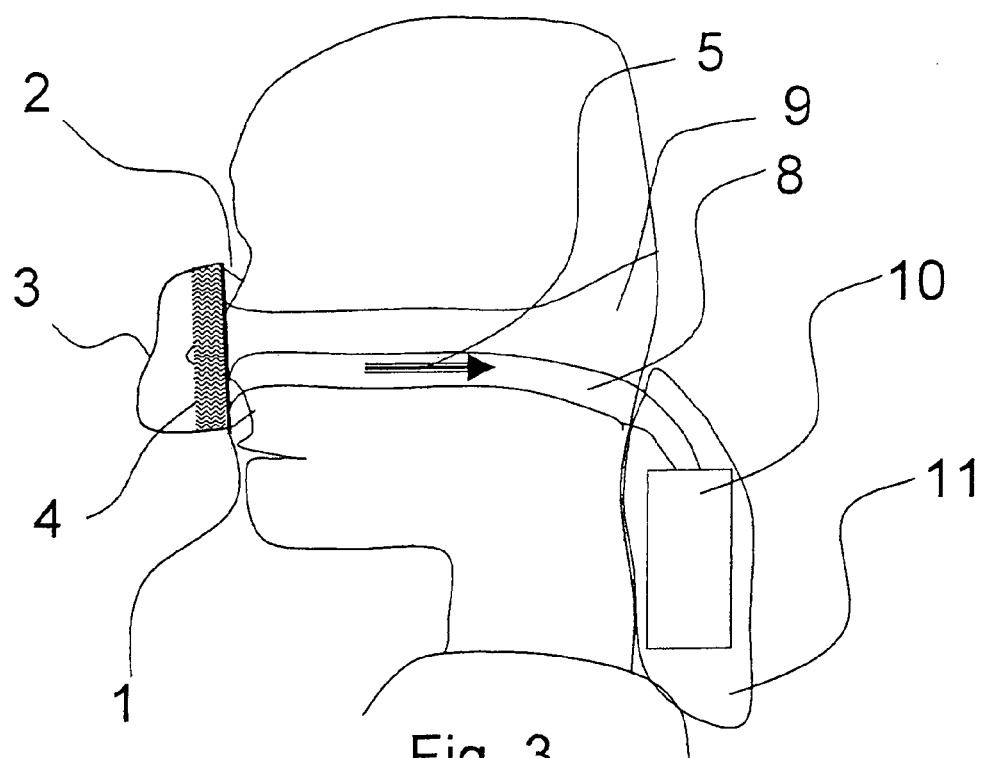
FIG. 3 is a side view of an overall device according to the present invention.

FIG. 3 shows a side view of an overall device according to the present invention. The suction volume flow is transported/delivered in the direction of arrow 5 through a lateral flexible tube 8' within the strap 9 of the mask to a CPAP device 10 within an adaptable padding 11 in the nape area. The breathing gas is fed under a slight overpressure into the interior of the breathing area mask body on the other side of the head through another flexible tube (not visible) within the strap.

Figure 4:
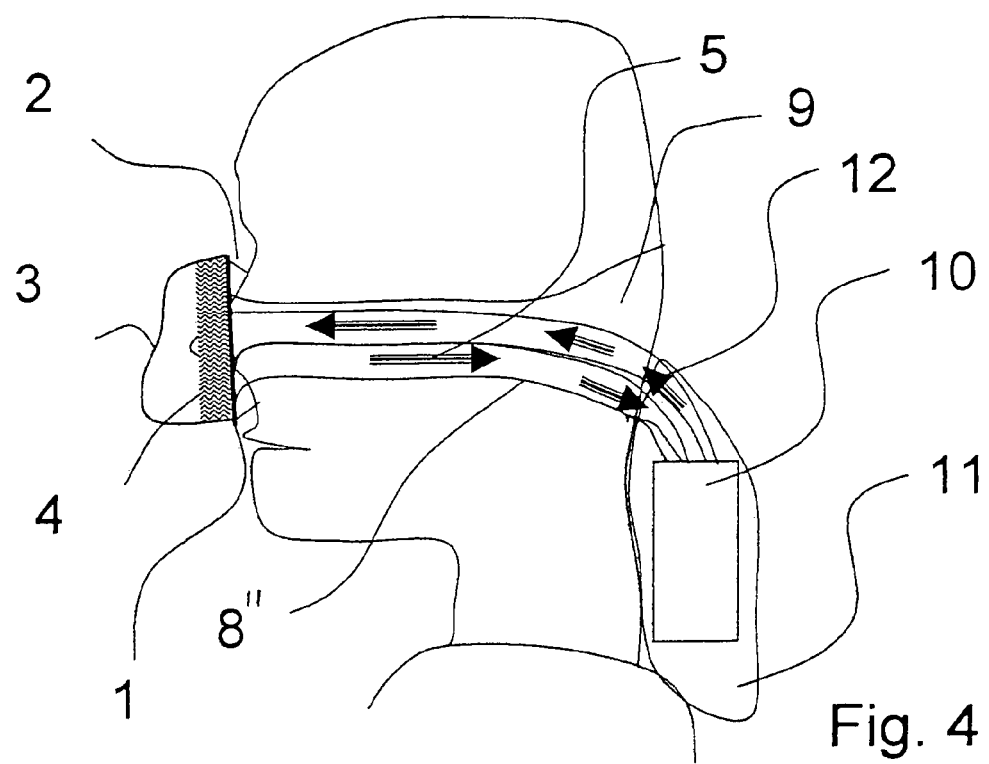
FIG. 4 is a side view of an overall device according to the present invention with double gas guide.

FIG. 4 shows a side view of an overall device according to the present invention in which the gas guide is provided in duplicate. The suction volume flow is transported/delivered in the direction of arrow 5 through bilateral channels 8" within the strap 9 of the mask to a breathing support device, here a CPAP device 10, within an adaptable padding 11 in the nape area. Additional channels 12, through which the breathing gas is fed under a slight overpressure into the interior breathing area of the mask body, extend in parallel to the channels 8". The channels 8" and 12 consist of textile pockets, which make it possible to put them on flat in case the head is in a lateral position, but they do have sufficient dimensional stability, so that complete closing of the suction channels 8" cannot take place due to the mere action of the vacuum occurring during the drawing in. If the head is supported on the side, the volume flows are transported/delivered extensively through the channels on the side of the head that is not supported. An especially high wear comfort is thus achieved with the highest possible level of reliability of operation.

While specific embodiments of the invention have been shown and described in detail to illustrate the application of the principles of the invention, it will be understood that the invention may be embodied otherwise without departing from such principles.

What is claimed is:

1. A breathing mask for a breathing support device to be connected to a patient, the breathing mask comprising:
   a mask body made of a material that is permeable to air at least in, said mask body having a suction area and a breathing area, said mask body being formed of said air permeable material in said suction area, said mask body including a non-permeable wall diving said suction area from said breathing area, said mask body having an interior side and an exterior side;
   a gas transport/delivery means for the transport/delivery of gas, the gas transport/delivery means being connectable to suction openings of the breathing support device and extending through the interior of the mask body, the gas transport/delivery means for the transport/delivery of gas ending at air-permeable areas of the mask body, said non-permeable wall guiding ambient air form said exterior side of said mask body, through said air permeable material of said suction area, and into said gas transport/delivery means.

2. A breathing mask in accordance with claim 1, wherein the gas transport/delivery means is fastened in an air-tight manner with respect to an interior space of the mask body and areas of the wall of the mask body, through which the ambient air can be drawn in, consist of a material that has a filter action for the air drawn in.

3. A breathing mask in accordance with claim 1, wherein the mask body is held by a strap, which encloses the gas transport/delivery means for guiding the air drawn in from the mask body to the breathing support device being carried close to the body.

4. A breathing mask in accordance with claim 3, wherein the strap comprises areas that have a multilayer design and at least two layers of the material of the strap that lie one on top of another are connected to one another such that they form a channel, which makes possible the transport/delivery of the air drawn in from the mask body to a breathing support device being carried close to the body.

5. A breathing mask in accordance with claim 4, wherein the cross section of the channel is variable.

6. A breathing mask in accordance with claim 3, wherein the strap and/or the mask body consist at least partly of a textile material.

7. A breathing mask in accordance with claim 3, wherein the strap comprises means for the transport/delivery of breathing gases from the breathing support device into an interior space of the mask body.

8. A breathing mask in accordance with claim 3, wherein the strap comprises at least two channels with one of said two channels configured to be arranged on each of different sides of the head of the user.

9. A breathing mask in accordance with claim 8, wherein the maximum cross section of the channels is large enough to enable the breathing gas supply to take place solely through the channels on one side of the head alone.

10. A breathing mask in accordance with claim 1, wherein the air-permeable areas of the wall of the mask body, through which ambient air can be drawn in, are arranged along the edge of the mask body in the vicinity of an area adapted to contact the user's face.

11. A breathing mask in accordance with claim 1, wherein at least one contiguous area of the wall of the mask body, through which ambient air can be drawn in, is limited against an interior space of the mask body by a flexible wall that is impermeable to air.

12. A breathing mask in accordance with claim 11, wherein the mask body comprises a shaping support frame, to which the material that forms the outer limitation of the mask body is attached, the support frame being located in the area of the air-impermeable flexible wall and the material that forms the outer limitation of the mask body.

13. A breathing mask in accordance with claim 1, wherein the mask body has at least air-permeable areas, through which expiratory breathing gases can escape into the environment.

14. A breathing mask in accordance with claim 1, wherein the means for the transport/delivery of gas is connected to the breathing support device, which is adapted to be worn in the nape or shoulder area.

15. A breathing mask arrangement comprising:

a mask body having a suction area and a breathing area, said mask body being formed of an air permeable material in said suction area, said mask body including a non-permeable wall dividing said suction area from said breathing area, said mask body having an interior side and an exterior side;

a first channel connected to said mask body and extending away from said mask body, said non-permeable wall guiding ambient air from said exterior side of said mask body, through said air permeable material of said suction area, and into said first channel;

a second channel connected to said mask body and in communication with said breathing area of said mask body.

16. An arrangement in accordance with claim 15, wherein:

said suction area is arranged around a circumference of said breathing area.

17. An arrangement in accordance with claim 15, wherein:

said mask body has a bowl shape, with said breathing area being in a center of said bowl shape, and said suction area being along an edge of said bowl shape.

18. A breathing mask arrangement comprising:

a mask body having a suction area and a breathing area, said mask body being formed of an air permeable material in said suction area, said mask body including a non-permeable wall dividing said suction area from said breathing area, said suction area being arranged around a circumference of said breathing area, said mask body having an interior side and an exterior side;

a channel connected to said mask body and extending away from said mask body, said non-permeable wall guiding ambient air from said exterior side of said mask body, through said air permeable material of said suction area, and into said channel.

19. An arrangement in accordance with claim 18, wherein:

said mask body has a bowl shape, with said breathing area being in a center of said bowl shape, and said suction area being along an edge of said bowl shape.

20. An arrangement in accordance with claim 18, further comprising:

another channel connected to said mask body and in communication with said breathing area of said mask body.

\* \* \* \* \*